(12) United States Patent
Melman

(10) Patent No.: US 8,521,253 B2
(45) Date of Patent: Aug. 27, 2013

(54) PROSTATE IMAGING

(75) Inventor: Haim Melman, Kfar-Saba (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 1236 days.

(21) Appl. No.: 11/976,852

(22) Filed: Oct. 29, 2007

(65) Prior Publication Data

US 2009/0112086 A1 Apr. 30, 2009

(51) Int. Cl.
A61B 5/05 (2006.01)

(52) U.S. Cl.
USPC ........... 600/407; 600/424; 600/437; 600/441; 600/443; 600/439

(58) Field of Classification Search
USPC .................. 600/407, 424, 437, 441, 443, 439
See application file for complete search history.

(56) References Cited

U.S. PATENT DOCUMENTS

| | | | |
|---|---|---|---|
| 630,611 A | 8/1899 | Knapp et al. |
| 2,776,377 A | 1/1957 | Anger |
| 3,340,866 A | 9/1967 | Nöller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |

(Continued)

FOREIGN PATENT DOCUMENTS

| | | |
|---|---|---|
| DE | 1516429 | 12/1969 |
| DE | 19814199 | 10/1999 |

(Continued)

OTHER PUBLICATIONS

Notice of Allowance Dated May 5, 2011 From the US Patent and Trademark Office Re.: U.S. Appl. No. 10/240,239.

(Continued)

Primary Examiner — Unsu Jung
Assistant Examiner — Joel Lamprecht

(57) ABSTRACT

A device for registering prostate images, the device comprises an elongate element suitable for insertion into a body passageway, the elongate element comprising at least one marker readable by an ultrasound probe and at least one marker readable by a gamma camera.

22 Claims, 7 Drawing Sheets
(7 of 7 Drawing Sheet(s) Filed in Color)

(56) References Cited

U.S. PATENT DOCUMENTS

| | | |
|---|---|---|
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledley |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hofgrefe et al. |
| 5,431,161 A | 7/1995 | Ryals et al. |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misik et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |

| Patent | Date | Name |
|---|---|---|
| 5,800,355 A | 9/1998 | Hasegawa |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,742 A | 9/1998 | Pearlman |
| 5,811,814 A | 9/1998 | Leone et al. |
| 5,813,985 A | 9/1998 | Carroll |
| 5,818,050 A | 10/1998 | Dilmanian et al. |
| 5,821,541 A | 10/1998 | Tümer |
| 5,825,031 A | 10/1998 | Wong et al. |
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A | 6/1999 | Judd et al. |
| 5,911,252 A | 6/1999 | Cassel |
| 5,916,167 A | 6/1999 | Kramer et al. |
| 5,916,197 A | 6/1999 | Reilly et al. |
| 5,920,054 A | 7/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,172,362 B1 | 1/2001 | Lingren et al. |
| 6,173,201 B1 | 1/2001 | Front |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 | 3/2001 | Torchilin et al. |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Tumer |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito |
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |

| Patent | Date | Inventor |
|---|---|---|
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tuemer |
| 6,425,174 B1 | 7/2002 | Riech |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engleson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,906,330 B2 | 6/2005 | Blevis et al. |
| D507,832 S | 7/2005 | Yanniello et al. |
| 6,915,170 B2 | 7/2005 | Engleson et al. |
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Tumer |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |

| | | | | | | |
|---|---|---|---|---|---|---|
| 6,974,443 B2 | 12/2005 | Reilly et al. | | 2003/0063787 A1 | 4/2003 | Natanzon et al. |
| 6,976,349 B2 | 12/2005 | Baldwin et al. | | 2003/0071219 A1 | 4/2003 | Motomura et al. |
| 6,984,222 B1 | 1/2006 | Hitchins et al. | | 2003/0081716 A1 | 5/2003 | Tumer |
| 6,985,870 B2 | 1/2006 | Martucci et al. | | 2003/0135388 A1 | 7/2003 | Martucci et al. |
| 6,988,981 B2 | 1/2006 | Hamazaki | | 2003/0136912 A1 | 7/2003 | Juni |
| 6,994,249 B2 | 2/2006 | Peterka et al. | | 2003/0144322 A1 | 7/2003 | Kozikowski et al. |
| 7,009,183 B2 | 3/2006 | Wainer et al. | | 2003/0147887 A1 | 8/2003 | Wang et al. |
| 7,011,814 B2 | 3/2006 | Suddarth et al. | | 2003/0158481 A1 | 8/2003 | Stotzka et al. |
| 7,012,430 B2 | 3/2006 | Misic | | 2003/0183226 A1 | 10/2003 | Brand et al. |
| 7,017,622 B2 | 3/2006 | Osborne et al. | | 2003/0189174 A1 | 10/2003 | Tanaka et al. |
| 7,018,363 B2 | 3/2006 | Cowan et al. | | 2003/0191430 A1 | 10/2003 | D'Andrea et al. |
| 7,019,783 B2 | 3/2006 | Kindem et al. | | 2003/0202629 A1 | 10/2003 | Dunham et al. |
| 7,025,757 B2 | 4/2006 | Reilly et al. | | 2003/0208117 A1 | 11/2003 | Shwartz et al. |
| 7,026,623 B2 | 4/2006 | Oaknin et al. | | 2003/0215122 A1 | 11/2003 | Tanaka |
| 7,043,063 B1 | 5/2006 | Noble et al. | | 2003/0215124 A1 | 11/2003 | Li |
| 7,102,138 B2 | 9/2006 | Belvis et al. | | 2003/0216631 A1 | 11/2003 | Bloch et al. |
| 7,103,204 B1 | 9/2006 | Celler et al. | | 2003/0219149 A1 | 11/2003 | Vailaya et al. |
| 7,127,026 B2 | 10/2006 | Amemiya et al. | | 2004/0003001 A1 | 1/2004 | Shimura |
| 7,142,634 B2 | 11/2006 | Engler et al. | | 2004/0010397 A1 | 1/2004 | Barbour et al. |
| 7,145,986 B2 | 12/2006 | Wear et al. | | 2004/0015075 A1 | 1/2004 | Kimchy et al. |
| 7,147,372 B2 | 12/2006 | Nelson et al. | | 2004/0021065 A1 | 2/2004 | Weber |
| 7,164,130 B2 | 1/2007 | Welsh et al. | | 2004/0044282 A1 | 3/2004 | Mixon et al. |
| 7,176,466 B2 | 2/2007 | Rousso et al. | | 2004/0051368 A1 | 3/2004 | Caputo et al. |
| 7,187,790 B2 | 3/2007 | Sabol et al. | | 2004/0054248 A1 | 3/2004 | Kimchy et al. |
| 7,217,953 B2 | 5/2007 | Carlson | | 2004/0054278 A1 | 3/2004 | Kimchy et al. |
| 7,256,386 B2 | 8/2007 | Carlson et al. | | 2004/0065838 A1 | 4/2004 | Tumer |
| 7,327,822 B2 | 2/2008 | Sauer et al. | | 2004/0075058 A1 | 4/2004 | Blevis et al. |
| 7,359,535 B2 | 4/2008 | Salla et al. | | 2004/0081623 A1 | 4/2004 | Eriksen et al. |
| 7,373,197 B2 | 5/2008 | Daighighian et al. | | 2004/0082918 A1 | 4/2004 | Evans et al. |
| 7,394,923 B2 | 7/2008 | Zou et al. | | 2004/0084340 A1 | 5/2004 | Morelle et al. |
| 7,444,010 B2 | 10/2008 | De Man | | 2004/0086437 A1 | 5/2004 | Jackson et al. |
| 7,468,513 B2 | 12/2008 | Charron et al. | | 2004/0101176 A1 | 5/2004 | Mendonca et al. |
| 7,490,085 B2 | 2/2009 | Walker et al. | | 2004/0101177 A1 | 5/2004 | Zahlmann et al. |
| 7,495,225 B2 | 2/2009 | Hefetz et al. | | 2004/0116807 A1 | 6/2004 | Amrami et al. |
| 7,502,499 B2 | 3/2009 | Grady | | 2004/0120557 A1 | 6/2004 | Sabol |
| 7,570,732 B2 | 8/2009 | Stanton et al. | | 2004/0122311 A1* | 6/2004 | Cosman ........................ 600/427 |
| 7,592,597 B2 | 9/2009 | Hefetz et al. | | 2004/0125918 A1 | 7/2004 | Shanmugaval et al. |
| 7,620,444 B2 | 11/2009 | Le et al. | | 2004/0138557 A1 | 7/2004 | Le et al. |
| 7,627,084 B2 | 12/2009 | Jabri et al. | | 2004/0144925 A1 | 7/2004 | Stoddart et al. |
| 7,671,331 B2 | 3/2010 | Hefetz | | 2004/0153128 A1 | 8/2004 | Suresh et al. |
| 7,672,491 B2 | 3/2010 | Krishnan et al. | | 2004/0162492 A1 | 8/2004 | Kobayashi |
| 7,680,240 B2 | 3/2010 | Manjeshwar et al. | | 2004/0171924 A1 | 9/2004 | Mire et al. |
| 7,705,316 B2 | 4/2010 | Rousso et al. | | 2004/0183022 A1 | 9/2004 | Weinberg |
| 7,826,889 B2 | 11/2010 | David et al. | | 2004/0184644 A1 | 9/2004 | Leichter et al. |
| 7,831,024 B2 | 11/2010 | Metzler et al. | | 2004/0193453 A1 | 9/2004 | Butterfield et al. |
| 7,835,927 B2 | 11/2010 | Schlotterbeck et al. | | 2004/0195512 A1 | 10/2004 | Crosetto |
| 7,894,650 B2 | 2/2011 | Weng et al. | | 2004/0204646 A1 | 10/2004 | Nagler et al. |
| 7,968,851 B2 | 6/2011 | Rousso et al. | | 2004/0205343 A1 | 10/2004 | Forth et al. |
| 8,158,951 B2 | 4/2012 | Bal et al. | | 2004/0210126 A1 | 10/2004 | Hajaj et al. |
| 2001/0016029 A1 | 8/2001 | Tumer | | 2004/0238743 A1 | 12/2004 | Gravrand et al. |
| 2001/0020131 A1 | 9/2001 | Kawagishi et al. | | 2004/0251419 A1 | 12/2004 | Nelson et al. |
| 2001/0035902 A1 | 11/2001 | Iddan et al. | | 2004/0253177 A1 | 12/2004 | Elmaleh et al. |
| 2001/0049608 A1 | 12/2001 | Hochman | | 2005/0001170 A1 | 1/2005 | Juni |
| 2002/0068864 A1 | 6/2002 | Bishop et al. | | 2005/0006589 A1 | 1/2005 | Joung et al. |
| 2002/0072784 A1 | 6/2002 | Sheppard, Jr. et al. | | 2005/0020898 A1 | 1/2005 | Vosniak et al. |
| 2002/0085748 A1 | 7/2002 | Baumberg | | 2005/0020915 A1 | 1/2005 | Bellardinelli et al. |
| 2002/0087101 A1 | 7/2002 | Barrick et al. | | 2005/0023474 A1 | 2/2005 | Persyk et al. |
| 2002/0099295 A1 | 7/2002 | Gil et al. | | 2005/0029277 A1 | 2/2005 | Tachibana |
| 2002/0099310 A1 | 7/2002 | Kimchy et al. | | 2005/0033157 A1* | 2/2005 | Klein et al. .................... 600/411 |
| 2002/0099334 A1 | 7/2002 | Hanson et al. | | 2005/0055174 A1 | 3/2005 | David et al. |
| 2002/0103429 A1 | 8/2002 | DeCharms | | 2005/0056788 A1 | 3/2005 | Juni |
| 2002/0103431 A1 | 8/2002 | Toker et al. | | 2005/0074402 A1 | 4/2005 | Cagnolini et al. |
| 2002/0145114 A1 | 10/2002 | Inoue et al. | | 2005/0107698 A1 | 5/2005 | Powers et al. |
| 2002/0148970 A1 | 10/2002 | Wong et al. | | 2005/0107914 A1 | 5/2005 | Engleson et al. |
| 2002/0165491 A1 | 11/2002 | Reilly | | 2005/0108044 A1 | 5/2005 | Koster |
| 2002/0168094 A1 | 11/2002 | Kaushikkar et al. | | 2005/0113945 A1 | 5/2005 | Engleson et al. |
| 2002/0168317 A1 | 11/2002 | Daighighian et al. | | 2005/0121505 A1 | 6/2005 | Metz et al. |
| 2002/0172405 A1 | 11/2002 | Schultz | | 2005/0131270 A1 | 6/2005 | Weil et al. |
| 2002/0179843 A1 | 12/2002 | Tanaka et al. | | 2005/0145797 A1 | 7/2005 | Oaknin et al. |
| 2002/0183645 A1 | 12/2002 | Nachaliel | | 2005/0148869 A1 | 7/2005 | Masuda |
| 2002/0188197 A1 | 12/2002 | Bishop et al. | | 2005/0149350 A1 | 7/2005 | Kerr et al. |
| 2002/0198738 A1 | 12/2002 | Osborne | | 2005/0156115 A1 | 7/2005 | Kobayashi et al. |
| 2003/0001098 A1 | 1/2003 | Stoddart et al. | | 2005/0173643 A1 | 8/2005 | Tumer |
| 2003/0001837 A1 | 1/2003 | Baumberg | | 2005/0187465 A1 | 8/2005 | Motomura et al. |
| 2003/0006376 A1 | 1/2003 | Tumer | | 2005/0198800 A1 | 9/2005 | Reich |
| 2003/0013950 A1 | 1/2003 | Rollo et al. | | 2005/0203389 A1 | 9/2005 | Williams |
| 2003/0013966 A1 | 1/2003 | Barnes et al. | | 2005/0205792 A1 | 9/2005 | Rousso et al. |
| 2003/0038240 A1 | 2/2003 | Weinberg | | 2005/0205796 A1 | 9/2005 | Bryman |
| 2003/0055685 A1 | 3/2003 | Cobb et al. | | 2005/0211909 A1 | 9/2005 | Smith |

| | | | | | |
|---|---|---|---|---|---|
| 2005/0215889 A1 | 9/2005 | Patterson, II | JP | 04-151120 | 5/1992 |
| 2005/0234424 A1 | 10/2005 | Besing et al. | JP | 06-109848 | 4/1994 |
| 2005/0247893 A1 | 11/2005 | Fu et al. | JP | 6-109848 | 4/1994 |
| 2005/0253073 A1 | 11/2005 | Joram et al. | JP | 07-059763 | 3/1995 |
| 2005/0261936 A1 | 11/2005 | Silverbrook et al. | JP | 07-141523 | 6/1995 |
| 2005/0261937 A1 | 11/2005 | Silverbrook et al. | JP | 08-292268 | 11/1996 |
| 2005/0261938 A1 | 11/2005 | Silverbrook et al. | JP | 10-260258 | 9/1998 |
| 2005/0266074 A1 | 12/2005 | Zilberstein et al. | JP | 11-072564 | 3/1999 |
| 2005/0277833 A1 | 12/2005 | Williams, Jr. | WO | WO 92/00402 | 1/1992 |
| 2005/0277911 A1 | 12/2005 | Stewart et al. | WO | WO 98/16852 | 4/1998 |
| 2005/0278066 A1 | 12/2005 | Graves et al. | WO | WO 99/03003 | 1/1999 |
| 2005/0288869 A1 | 12/2005 | Kroll et al. | WO | WO 99/30610 | 6/1999 |
| 2006/0000983 A1 | 1/2006 | Charron et al. | WO | WO 99/39650 | 8/1999 |
| 2006/0033028 A1 | 2/2006 | Juni | WO | WO 00/10034 | 2/2000 |
| 2006/0036157 A1 | 2/2006 | Tumer | WO | WO 00/18294 | 4/2000 |
| 2006/0072799 A1 | 4/2006 | McLain | WO | WO 00/22975 | 4/2000 |
| 2006/0074290 A1 | 4/2006 | Chen et al. | WO | WO 00/31522 | 6/2000 |
| 2006/0109950 A1 | 5/2006 | Arenson et al. | WO | WO 00/38197 | 6/2000 |
| 2006/0122503 A1 * | 6/2006 | Burbank et al. ............ 600/431 | WO | WO 01/89384 | 11/2001 |
| 2006/0145081 A1 | 7/2006 | Hawman | WO | WO 02/16965 | 2/2002 |
| 2006/0160157 A1 | 7/2006 | Zuckerman | WO | WO 02/058531 | 8/2002 |
| 2006/0237652 A1 | 10/2006 | Kimchy et al. | WO | WO 02/075357 | 9/2002 |
| 2006/0257012 A1 | 11/2006 | Kaufman et al. | WO | WO 03/073938 | 9/2003 |
| 2007/0116170 A1 | 5/2007 | De Man et al. | WO | WO 03/086170 | 10/2003 |
| 2007/0133852 A1 | 6/2007 | Collins et al. | WO | WO 2004/004787 | 1/2004 |
| 2007/0156047 A1 | 7/2007 | Nagler et al. | WO | WO 2004/032151 | 4/2004 |
| 2007/0166227 A1 | 7/2007 | Liu et al. | WO | WO 2004/042546 | 5/2004 |
| 2007/0189436 A1 | 8/2007 | Goto et al. | WO | WO 2004/113951 | 12/2004 |
| 2007/0194241 A1 | 8/2007 | Rousso et al. | WO | WO 2005/002971 | 1/2005 |
| 2007/0265230 A1 | 11/2007 | Rousso et al. | WO | WO 2005/059592 | 6/2005 |
| 2008/0001090 A1 | 1/2008 | Ben-Haim et al. | WO | WO 2005/059840 | 6/2005 |
| 2008/0029704 A1 | 2/2008 | Hefetz et al. | WO | WO 2005/067383 | 7/2005 |
| 2008/0033291 A1 | 2/2008 | Rousso et al. | WO | WO 2005/104939 | 11/2005 |
| 2008/0036882 A1 | 2/2008 | Uemura et al. | WO | WO 2005/118659 | 12/2005 |
| 2008/0039721 A1 | 2/2008 | Shai et al. | WO | WO 2005/119025 | 12/2005 |
| 2008/0042067 A1 | 2/2008 | Rousso et al. | WO | WO 2006/042077 | 4/2006 |
| 2008/0128626 A1 | 6/2008 | Rousso et al. | WO | WO 2006/051531 | 5/2006 |
| 2008/0137938 A1 | 6/2008 | Zahniser | WO | WO 2006/054296 | 5/2006 |
| 2008/0230702 A1 | 9/2008 | Rousso et al. | WO | WO 2006/075333 | 7/2006 |
| 2008/0230705 A1 | 9/2008 | Rousso et al. | WO | WO 2006/129301 | 12/2006 |
| 2008/0237482 A1 | 10/2008 | Shahar et al. | WO | WO 2007/010534 | 1/2007 |
| 2008/0260228 A1 | 10/2008 | Dichterman et al. | WO | WO 2007/010537 | 1/2007 |
| 2008/0260637 A1 | 10/2008 | Dickman | WO | WO 2007/054935 | 5/2007 |
| 2008/0277591 A1 | 11/2008 | Shahar et al. | WO | WO 2007/074467 | 7/2007 |
| 2009/0001273 A1 | 1/2009 | Hawman | WO | WO 2008/010227 | 1/2008 |
| 2009/0018412 A1 | 1/2009 | Schmitt | WO | WO 2008/075362 | 6/2008 |
| 2009/0078875 A1 | 3/2009 | Rousso et al. | | | |
| 2009/0152471 A1 | 6/2009 | Rousso et al. | | | |
| 2009/0190807 A1 | 7/2009 | Rousso et al. | | | |
| 2009/0201291 A1 | 8/2009 | Ziv et al. | | | |
| 2009/0236532 A1 | 9/2009 | Frach et al. | | | |
| 2009/0304582 A1 | 12/2009 | Rousso et al. | | | |
| 2010/0006770 A1 | 1/2010 | Balakin | | | |
| 2010/0021378 A1 | 1/2010 | Rousso et al. | | | |
| 2010/0102242 A1 | 4/2010 | Burr et al. | | | |
| 2010/0140483 A1 | 6/2010 | Rousso et al. | | | |
| 2010/0202664 A1 | 8/2010 | Busch et al. | | | |
| 2010/0245354 A1 | 9/2010 | Rousso et al. | | | |
| 2012/0106820 A1 | 5/2012 | Rousso et al. | | | |
| 2012/0248320 A1 | 10/2012 | Wangerin et al. | | | |
| 2012/0326034 A1 | 12/2012 | Sachs et al. | | | |
| 2013/0114792 A1 | 5/2013 | Zilberstein et al. | | | |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |

OTHER PUBLICATIONS

Response Dated Jul. 8, 2010 to Communication Pursuant to Article 94(3) EPC of Mar. 8, 2010 From the European Patent Office Re.: Application No. 06832278.3.

Examination Report Dated Jun. 22, 2011 From the Government of India, Patent Office, Intellectual Property Building Re. Application No. 2963/CHENP/2006.

Official Action Dated Mar. 9, 2011 From the US Patent and Trademark Office Re.: U.S. Appl. No. 10/616,301.

Response Dated Jun. 7, 2011 to Official Action of Mar. 9, 2011 From the US Patent and Trademark Office Re.: U.S. Appl. No. 10/616,301.

Response Dated Jun. 28, 2011 to Official Action of Dec. 28, 2010 From the US Patent and Trademark Office Re.: U.S. Appl. No. 11/607,075.

Communication Pursuant to Article 94(3) EPC Dated May 12, 2010 From the European Patent Office Re.: Application No. 06809851.6.

Communication Pursuant to Article 94(3) EPC Dated Apr. 16, 2010 From the European Patent Office Re. Application No. 01951883.6.

Communication Pursuant to Article 96(2) EPC Dated Jun. 19, 2006 From the European Patent Office Re.: Application No. 03810570.6.

Communication Relating to the Results of the Partial International Search Dated Apr. 18, 2007 From the International Searching Authority of the Patent Cooperation Treaty Re.: Application No. PCT/IL2006/001291.

Communication Relating to the Results of the Partial International Search Dated May 21, 2008 From the International Searching Authority of the Patent Cooperation Treaty Re.: Application No. PCT/IL2007/001588.

International Preliminary Report on Patentability Dated Apr. 16, 2009 From the International Bureau of WIPO Re.: Applicaiton No. PCT/IL2007/000918.
International Preliminary Report on Patentability Dated Jan. 22, 2009 From the International Bureau of WIPO Re.: Application No. PCT/IL2006/000834.
International Search Report Dated Jul. 25, 2008 From the International Searching Authority of the Patent Cooperation Treaty Re.: Application No. PCT/IL2007/001588.
International Search Report Dated Aug. 3, 2006 From the International Searching Authority of the Patent Cooperation Treaty Re.: Application No. PCT/IL05/001173.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Mar. 18, 2004 From the International Searching Authority of the Patent Cooperation Treaty Re.: Application No. PCT/IL03/00917.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Notice of Allowance Dated Sep. 17, 2009 From the US Patent and Trademark Office Re.: U.S. Appl. No. 10/533,568. Suppl. IDS VIII.
Notice of Allowance Dated Jul. 22, 2010 From the US Patent and Trademark Office Re.: U.S. Appl. No. 11/794,799.
Notice of Allowance Dated Aug. 25, 2010 From the US Patent and Trademark Office Re. U.S. Appl. No. 11/980,617.
Office Action Dated Dec. 2, 2007 From the Israeli Patent Office Re.: Application No. 158442.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Apr. 8, 2010 From the US Patent and Trademark Office Re.: U.S. Appl. No. 11/980,690.
Official Action Dated Apr. 9, 2010 From the US Patent and Trademark Office Re.: U.S. Appl. No. 11/798,017.
Official Action Dated Aug. 10, 2007 From the US Patent and Trademark Office Re.: U.S. Appl. No. 10/836,223.
Official Action Dated Apr. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/725,316.
Official Action Dated Jan. 17, 2006 From the United States Patent and Trademark Office Re.: U.S. Appl. No. 11/034,007.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Apr. 28, 2010 From the US Patent and Trademark Office Re.: U.S. Appl. No. 10/616,301.
Official Action Dated Sep. 30, 2008 From the US Patent and Trademark Office Re.: U.S. Appl. No. 10/616,301.

Response Dated Jul. 1, 2010 to Official Action of Mar. 2, 2010 From the US Patent and Trademark Office Re.: U.S. Appl. No. 10/836,223.
Response Dated Jul. 1, 2010 to Official Action of Mar. 2, 2010 From the US Patent and Trademark Office Re.: U.S. Appl. No. 11/980,617.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Response Dated Jul. 8, 2010 to Official Action of Apr. 9, 2010 From the US Patent and Trademark Office Re.: U.S. Appl. No. 11/798,017.
Response Dated Sep. 8, 2010 to Communication Pursuant to Article 94(3) EPC Dated May 12, 2010 From the European Patent Office Re.: Application No. 06809851.6.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Response Dated Aug. 16, 2010 to Communication Pursuant to Article 94(3) EPC of Apr. 16, 2010 From the European Patent Office Re. Application No. 01951883.6.
Response Dated Jun. 23, 2010 to Official Action of Feb. 23, 2010 From the US Patent and Trademark Office Re.: U.S. Appl. No. 09/641,973.
Response Dated Aug. 25, 2010 to Official Action of Jul. 27, 2010 From the US Patent and Trademark Office Re.: U.S. Appl. No. 10/616,307.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Jul. 2, 2007 From the international Searching Authority of the Patent Cooperation Treaty Re.: Application No. PCT/IL2006/001291.
Written Opinion Dated Oct. 10, 2006 From the International Searching Authority of the Patent Cooperation Treaty Re.: Application No. PCT/IL06/00059.
Written Opinion Dated Mar. 23, 2006 From the International Searching Authority of the Patent Cooperation Treaty Re.: Application No. PCT/IL05/00572.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Gugnin et al "Radiocapsule for Recording the Ionizing Radiation in the Gastrointestinal Tract", UDC 615.417:616.34-005.1-073.916-71

(All-Union Scientific-Research Institute of medical Instrument Design, Moscow. Translated from Meditsinskaya Tekhnika, 1:21-25, Jan.-Feb. 1972).
Hayakawa et al. "A PET-MRI Registration Technique for PET Studies of the Rat Brain", Nuclear Medicine & Biology, 27: 121-125, 2000. p. 121, col. 1.
Kojima et al. "Quantitative Planar Imaging Method for Measurement of Renal Activity by Using a Conjugate-Emission Image and Transmission Data", Medical Physics, 27(3): 608-615, 2000. p. 608.
Lavallée et al. "Building a Hybrid Patient's Model for Augmented Reality in Surgery: A Registration Problem", Computing in Biological Medicine, 25(2): 149-164, 1995.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Pardridge et al. "Tracer Kinetic Model of Blood-Brain Barrier Transport of Plasma Protein-Bound Ligands", Journal of Clinical Investigation, 74: 745-752, 1984.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Zaidi et al. "MRI-Guided Attenuation Correction in 3D Brain PET", Neuroimage Human Brain Mapping 2002 Meeting, 16(2): Abstract 504, Jun. 2002.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Communication Pursuant to Article 94(3) EPC Dated Mar. 2, 2011 From the European Patent Office Re.: Application No. 06756259.5.
Notice of Allowance Dated Nov. 15, 2010 From the US Patent and Trademark Office Re. U.S. Appl. No. 10/616,301.
Notice of Non-Compliant Amendment Dated Feb. 14, 2011 From the US Patent and Trademark Office Re.: U.S. Appl. No. 10/616,307.
Response Dated Feb. 10, 2011 to Notice of Allowance of Nov. 15, 2010 From the US Patent and Trademark Office Re. U.S. Appl. No. 10/616,301.
Lin et al. "Improved Sensor Pills for Physiological Monitoring", NASA Technical Brief, JPL New Technology Report, NPO-20652, 25(2), 2000.
Mettler et al. "Legal Requirements and Radiation Safety", Essentials of Nuclear Medicine Imaging, 2nd Ed., Chap.13: 323-331, 1985.
Final OA dated Jul. 12, 2007.
Invitation to Pay Additional Fees.
Invitation to pay additional fees dated Apr. 18, 2007.
OA dated Sep. 4, 2008.
OA of Jun. 1, 2006.
OA of Aug. 10, 2007.
OA of Jan. 17, 2006.
OA of Jun. 19, 2006.
OA of Jan. 7, 2009.
Official Action Dated May 3, 2007 From the US Patent and Trademark Office Re.: U.S. Appl. No. 10/240,239.
Official Action Dated Oct. 7, 2008 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Apr. 15, 2008 From the US Patent and Trademark Office Re.: U.S. Appl. No. 09/727,464.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Apr. 20, 2006 From the US Patent and Trademark Office Re.: U.S. Appl. No. 10/240,239.
Official Action Dated Dec. 23, 2008 From the US Patent and Trademark Office Re.: U.S. Appl. No. 09/727,464.
Official Action Dated Jun. 23, 2006 From the US Patent and Trademark Office Re.: U.S. Appl. No. 09/727,464.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Official Action Dated Jan. 7, 2009 From the US Patent and Trademark Office Re.: U.S. Appl. No. 10/616,307.
Official Action Dated Dec. 16, 2008 From the US Patent and Trademark Office Re.: U.S. Appl. No. 10/343,792.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Aug. 14, 2008 to Official Action of Apr. 15, 2008 From the US Patent and Trademark Office Re.: U.S. Appl. No. 09/727,464.
Response Dated Nov. 25, 2005 to Office Action of May 13, 2005 From the Patent Office of the People's Republic of China Re.: Application No. 1817689.5.
Response to the International Search Report and the Written Opinion of Oct. 10, 2006 From the International Searching Authority Re.: Appliction No. PCT/IL06/00059.

Summons to Attend Oral Proceedings Pursuant to Rule 115(1) EPC Dated Jan. 16, 2009 From the European Patent Office Re.: Application No. 03810570.6.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Kinahan et al. "Attenuation Correction for a Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Notice of Allowance Dated Jun. 23, 2011 From the US Patent and Trademark Office Re.: U.S. Appl. No. 10/616,301.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Sep. 2, 2009 From the US Patent and Trademark Office Re.: U.S. Appl. No. 10/343,792.
Official Action Dated Aug. 11, 2009 From the US Patent and Trademark Office Re.: U.S. Appl. No. 09/641,973.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Sep. 16, 2009 From the US Patent and Trademark Office Re.: U.S. Appl. No. 09/727,464.
Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Response Dated Nov. 16, 2009 to Official Action of Jul. 15, 2009 From the US Patent and Trademark Office Re.: U.S. Appl. No. 10/616,301.
Supplementary Partial European Search Report and the European Search Opinion Dated Oct. 16, 2009 From the European Patent Office Re.: Application No. 06756259.5.

Communication pursuant to Article 96(2) EPC Dated Aug. 30, 2007 From the European Patent Office Re.: Application No. 03810570.6.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated May 11, 2006 From the International Searching Authority of the Patent Cooperation Treaty Re.: Application No. PCT/IL05/001215.
International Search Report Dated Mar. 23, 2006 From the International Searching Authority of the Patent Cooperation Treaty Re.: Application No. PCT/IL05/00572.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jul. 17, 2007 From the Israeli Patent Office Re.: Application No. 154323.
Written Opinion Dated May 24, 2007 From the International Searching Authority of the Patent Cooperation Treaty Re.: Application No. PCT/1IL05/00575.
Written Opinion Dated Mar. 26, 2007 From the International Searching Authority of the Patent Cooperation. Treaty Re.: Application No. PCT/IL05/00394.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.

Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Iann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Response Dated Mar. 3, 2011 to Notice of Non-Compliant Amendment of Feb. 14, 2011 From the US Patent and Trademark Office Re.: U.S. Appl. No. 10/616,307.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 11, 2010 From the US Patent and Trademark Office Re.: U.S. Appl. No. 11/607,075.
Official Action Dated Mar. 19, 2010 From the US Patent and Trademark Office Re.: U.S. Appl. No. 10/240,239.
Official Action Dated Feb. 23, 2010 From the US Patent and Trademark Office Re.: U.S. Appl. No. 09/641,973.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.

Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "Simultaneous Reconstruction and Motion Estimation for Gated Cardiac ECT", IEEE Transactions on Nuclear Science, XP011077797, 49(5): 23442349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Communication Pursuant to Article 93(3) EPC Dated Mar. 8, 2010 From the European Patent Office Re.: Application No. 06832278.3.
International Search Report Dated Oct. 10, 2006 From the International Searching Authority of the Patent Cooperation Treaty Re.: Application No. PCT/IL06/00059.
Written Opinion Dated Aug. 3, 2006 From the International Searching Authority of the Patent Cooperation Treaty Re.: Application No. PCT/IL05/001173.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.
Bromiley et al. "Attenuation Correction in PET Using Consistency Conditions and A Three-Dimensional Template", IEEE Transactions on Nuclear Science, 48(4): 1371-1377, 2001. p. 1376, col. 2, § 2.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Hassan et al. "A Radiotelemetry Pill for the Measurement of Ionising Radiation Using a Mercuric Iodide Detector", Physics in Medicine and Biology, 23(2): 302-308, 1978.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry 89(3-4): 349-352, 2000.
Jessup "Tumor Markers—Prognostic and Therapeutic Implications for Colorectal Carcinoma", Surgical Oncology, 7: 139-151, 1998.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Mori et al. "Overexpression of Matrix Metalloproteinase-7mRNA in Human Colon Carcinomas", Cancer, 75: 1516-1519, 1995.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Piperno et al. "Breast Cancer Screening by Impedance Measurements", Frontiers Med. Biol. Engng., 2(2): 11-17, 1990.
Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedence Monitoring During CT-Guided Stereotactic Surgery: Relative Value in Cystic and Solid Lesions", British Journal of Neurosurgery, 6: 439-444, 1992.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Zhang et al. "An Innovative High Efficiency and High Resolution Probe for Prostate Imaging", The Journal of Nuclear Medicine, 68: 18, 2000. Abstract.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
McJilton et al. "Protein Kinase Cε Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Communication Pursuant to Article 94(3) EPC Dated Jul. 22, 2009 From the European Patent Office Re.: Application No. 06809851.6.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Jul. 15, 2009 From the US Patent and Trademark Office Re.: U.S. Appl. No. 10/616,301.
Official Action Dated Jul. 20, 2009 From the US Patent and Trademark Office Re.: U.S. Appl. No. 11/980,617.
Response Dated Mar. 13, 2008 to Official Action of Dec. 13, 2007 From the US Patent and Trademark Office Re.: U.S. Appl. No. 10/616,301.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Oct. 31, 2007 to Official Action of Jul. 12, 2007 From the US Patent and Trademark Office Re.: U.S. Appl. No. 10/616,301.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
Official Action Dated Jan. 31, 2011 From the US Patent and Trademark Office Re. U.S. Appl. No. 11/667,793.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Response Dated Mar. 24, 2011 to Official Action of Dec. 8, 2010 From the US Patent and Trademark Office Re.: U.S. Appl. No. 09/641,973.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.
Interview Summary Dated May 31, 2011 From the US Patent and Trademark Office Re. U.S. Appl. No. 10/616,301.
Response Dated Jun. 1, 2010 to Official Action of Mar. 1, 2010 From the US Patent and Trademark Office Re.: U.S. Appl. No. 11/794,799.
Official Action Dated Jun. 28, 2011 From the US Patent and Trademark Office Re. U.S. Appl. No. 11/628,074.
Response Dated Mar. 8, 2011 to Official Action of Dec. 8, 2010 From the US Patent and Trademark Office Re.: U.S. Appl. No. 11/980,690.
Official Action Dated Jul. 12, 2011 From the US Patent and Trademark Office Re.: U.S. Appl. No. 09/641,973.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.
Response dated Sep. 1, 2010 to Official Action of Aug. 3, 2010 From the US Patent and Trademark Office Re.: U.S. Appl. No. 11/980,690.
Official Action Dated Jan. 19, 2012 From the US Patent and Trademark Office Re. U.S. Appl. No. 11/667,793.

Official Action Dated Jan. 23, 2012 From the US Patent and Trademark Office Re. U.S. Appl. No. 12/087,150.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Toennies et al. "Scatter Segmentation in Dynamic SPECT Images Using Principal Component Analysis", Progress in Biomedical Optics and Imaging, 4(23): 507-516, 2003.
Notice of Allowance Dated Feb. 2, 2012 From the US Patent and Trademark Office Re. U.S. Appl. No. 11/628,074.
Notice of Panel Decision From Pre-Appeal Brief Review Dated Feb. 29, 2012 From the US Patent and Trademark Office Re.: U.S. Appl. No. 10/836,223.
Official Action Dated Mar. 1, 2012 From the US Patent and Trademark Office Re.: U.S. Appl. No. 10/616,307.
Official Action Dated Dec. 22, 2011 From the US Patent and Trademark Office Re. U.S. Appl. No. 12/514,785.
Official Action Dated Feb. 28, 2012 From the US Patent and Trademark Office Re.: U.S. Appl. No. 09/641,973.
Official Action Dated Mar. 6, 2012 From the US Patent and Trademark Office Re. U.S. Appl. No. 12/792,856.
Office Action Dated Jul. 17, 2007 From the Israeli Patent Office Re.: Application No. 154323 and Its Translation Into English.
Restriction Official Action Dated Apr. 13, 2012 From the US Patent and Trademark Office Re. U.S. Appl. No. 11/989,223.
Official Action Dated Apr. 16, 2012 From the US Patent and Trademark Office Re.: U.S. Appl. No. 10/836,223.
Communication Pursuant to Article 94(3) EPC Dated Jun. 11, 2012 From the European Patent Office Re.: Application No. 06756259.5.
Communication Pursuant to Article 94(3) EPC Dated May 12, 2010 From the European Patent Office Re. Application No. 06809851.6.
Communication Pursuant to Article 94(3) EPC Dated May 29, 2012 From the European Patent Office Re. Application No. 05803689.8.
Communication Under Rule 71(3) EPC Dated May 30, 2012 From the European Patent Office Re.: Application No. 02716285.8.
international Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Search Report Dated Jul. 1, 2008 From the International Searching Authority Re. Application No. PCT/IL2006/000834.
International Search Report Dated Jul. 2, 2007 From the International Searching Authority Re. Application No. PCT/IL2006/001291.
International Search Report Dated Aug. 3, 2006 From the International Searching Authority Re. Application No. PCT/IL2005/001173.
International Search Report Dated Oct. 15, 2008 From the International Searching Authority Re. Application No. PCT/2007/000918.
Official Action Dated Nov. 1, 2010 From the US Patent and Trademark Office Re. U.S. Appl. No. 12/728,383.
Official Action Dated Mar. 2, 2010 From the US Patent and Trademark Office Re. U.S. Appl. No. 11/980,617.
Official Action Dated Dec. 8, 2010 From the US Patent and Trademark Office Re. U.S. Appl. No. 11/980,690.
Official Action Dated Apr. 9, 2010 From the US Patent and Trademark Office Re. U.S. Appl. No. 11/798,017.
Official Action Dated Aug. 13, 2008 From the US Patent and Trademark Office Re. U.S. Appl. No. 11/769,826.
Official Action Dated Feb. 16, 2012 From the US Patent and Trademark Office Re. U.S. Appl. No. 11/747,378.
Official Action Dated May 18, 2012 From the US Patent and Trademark Office Re. U.S. Appl. No. 11/989,223.
Official Action Dated Apr. 20, 2011 From the US Patent and Trademark Office Re. U.S. Appl. No. 11/798,017.
Official Action Dated Dec. 20, 2011 From the US Patent and Trademark Office Re. U.S. Appl. No. 12/309,479.
Official Action Dated Sep. 21, 2009 From the US Patent and Trademark Office Re. U.S. Appl. No. 11/798,017.
Official Action Dated May 23, 2011 From the US Patent and Trademark Office Re. U.S. Appl. No. 11/980,690.
Official Action Dated Sep. 30, 2010 From the US Patent and Trademark Office Re. U.S. Appl. No. 11/798,017.
Bracco Diagnostics "Cardiotec®: Kit for the Preparation of Technetium Tc 99m, Teboroxime For Diagnostic Use", Braco Diagnostics Inc., Product Sheet 2P• Jul. 2003.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dillman "Radiolabeled Anti-CD20 Monoclonal Antibodies for the Treatment of B-Cell Lymphoma", Journal of Clinical Oncology, 20(16): 3545-3557, Aug. 15, 2002.
Mallinckrodt "Kit for the Preparation of Technetium Tc 99m Sestamibi Injection", Mallinckrodt Inc., Product Sheet, 2 P., Sep. 8, 2008.
Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.
Saltz et al. "Interim Report of Randomized Phase II Trial of Cetuximab/Bevacizumab/Trinotecan (CBI) Versus Cetuximab/Bevacizumab (CB) in Irinotecan-Refractory Colorectal Cancer", Gastrointestinal Cancer Symposium, Hollywood, FL., USA, Jan. 27-29, 2005, American Society of Clinical Oncology, Abstract 169b, 4 P., 2005.
Sands et al. "Methods for the Study of the Metabolism of Radiolabeled Monoclonal Antibodies by Liver and Tumor", The Journal of Nuclear Medicine, 28: 390-398, 1987.
Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Official Action Dated Jun. 21, 2012 From the US Patent and Trademark Office Re. U.S. Appl. No. 12/309,479.
Official Action Dated Jul. 30, 2012 From the US Patent and Trademark Office Re.: U.S. Appl. No. 11/980,683.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Official Action Dated Aug. 2, 2012 From the US Patent and Trademark Office Re. U.S. Appl. No. 12/087,150.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Restriction Official Action Dated Aug. 16, 2012 From the US Patent and Trademark Office Re. U.S. Appl. No. 12/448,473.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Official Action Dated Aug. 31, 2012 From the US Patent and Trademark Office Re. U.S. Appl. No. 11/980,653.
Communication Pursuant to Article 94(3) EPC Dated Sep. 22, 2011 From the European Patent Office Re. Application No. 06756258.7.
Notice of Allowance Dated Sep. 16, 2011 From the US Patent and Trademark Office Re.: U.S. Appl. No. 11/607,075.
Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.

Response Dated Sep. 12, 2011 to Official Action of Jul. 11, 2011 From the US Patent and Trademark Office Re.: U.S. Appl. No. 11/980,683.
Response Dated Sep. 20, 2011 to Official Action of Apr. 20, 2011 From the Its Patent and Trademark Office Re.: U.S. Appl. No. 11/798,017.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With a Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
Response Dated Oct. 14, 2011 to Supplementary European Search Report and the European Search Opinion of Mar. 16, 2011 From the European Patent Office Re. Application No. 05803689.8.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Supplemental Notice of Allowability Dated Oct. 24, 2011 From the US Patent and Trademark Office Re.: U.S. Appl. No. 11/607,075.
Notice of Allowance Dated Oct. 11, 2011 From the US Patent and Trademark Office Re. U.S. Appl. No. 11/988,926.
Response Dated Oct. 14, 2011 to Communication Pursuant to Rules 70(2) and 70a(2) EPC of Apr. 4, 2011 From the European Patent Office Re. Application No. 05803689.8.
Restriction Official Action Dated Nov. 8, 2011 From the US Patent and Trademark Office Re. U.S. Appl. No. 12/309,479.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Restriction Official Action Dated Nov. 15, 2011 From the US Patent and Trademark Office Re. U.S. Appl. No. 11/980,683.
Official Action Dated Dec. 15, 2011 From the US Patent and Trademark Office Re.: U.S. Appl. No. 10/343,792.
Response Dated Nov. 13, 2011 to Official Action of Sep. 12, 2011 From the US Patent and Trademark Office Re. U.S. Appl. No. 11/980,653.
Response Dated Dec. 29, 2011 to Office Action of Jul. 17, 2007 From the Israeli Patent Office Re.: Application No. 154323.
Berman et al. "Dual-Isotope Myocardial Perfusion SPECT With Rest Thallium-201 and Stress Tc-99m Sestamibi", Cardiology Clinics, 12(2): 261-270, May 1994.
DeGrado et al. "Topics in Integrated Systems Physiology. Tracer Kinetic Modeling in Nuclear Cardiology", Journal of Nuclear Cardiology, 7: 686-700, 2000.
Links "Advances in SPECT and PET Imaging", Annals in Nuclear Medical Science, 13(2): 107-120, Jun. 2000.
Response Dated Dec. 8, 2011 to Restriction Official Action of Nov. 8, 2011 From the US Patent and Trademark Office Re. U.S. Appl. No. 12/309,479.
Communication Pursuant to Article 94(3) EPC Dated Nov. 18, 2011 From the European Patent Office Re. Application No. 05803689.8.
Response Dated Nov. 14, 2011 to Official Action of Jul. 12, 2011 From the US Patent and Trademark Office Re.: U.S. Appl. No. 09/641,973.
Response Dated Nov. 23, 2011 to Official Action of May 23, 2011 From the US Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.

Response Dated Nov. 28, 2011 to Official Action of Jun. 28, 2011 From the US Patent and Trademark Office Re. U.S. Appl. No. 11/628,074.
Notice of Allowance Dated Sep. 28, 2012 From the US Patent and Trademark Office Re. U.S. Appl. No. 12/792,856.
Applicant-Initiated Interview Summary Dated Jan. 28, 2013 From the US Patent and Trademark Office Re.: U.S. Appl. No. 11/798,017.
Official Action Dated Feb. 7, 2013 From the US Patent and Trademark Office Re. U.S. Appl. No. 11/980,653.
Advisory Action Before the Filing of an Appeal Brief Dated Feb. 26, 2013 From the US Patent and Trademark Office Re. U.S. Appl. No. 12/514,785.
Notice of Allowance Dated Feb. 21, 2013 From the US Patent and Trademark Office Re. U.S. Appl. No. 11/798,017.
Communication Under Rule 71(3) EPC Dated Feb. 26, 2013 From the European Patent Office Re. Application No. 06756259.5.
Official Action Dated Feb. 22, 2013 From the US Patent and Trademark Office Re.: U.S. Appl. No. 10/616,307.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Communication Pursuant to Article 94(3) EPC Dated Nov. 12, 2012 From the European Patent Office Re. Application No. 06756258.7.
Communication Pursuant to Article 94(3) EPC Dated Oct. 26, 2012 From the European Patent Office Re. Application No. 05803689.8.
Notice of Allowance Dated Nov. 15, 2012 From the US Patent and Trademark Office Re.: U.S. Appl. No. 11/980,683.
Notice of Allowance Dated Feb. 23, 2011 From the US Patent and Trademark Office Re.: U.S. Appl. No. 12/728,383.
Notice of Allowance Dated Dec. 26, 2012 From the US Patent and Trademark Office Re.: U.S. Appl. No. 11/980,690.
Notice of Allowance Dated Oct. 26, 2012 From the US Patent and Trademark Office Re. U.S. Appl. No. 12/514,785.
Official Action Dated Oct. 7, 2011 From the US Patent and Trademark Office Re. U.S. Appl. No. 11/750,057.
Official Action Dated Oct. 7, 2011 From the US Patent and Trademark Office Re. U.S. Appl. No. 11/932,872.
Official Action Dated Oct. 10, 2012 From the US Patent and Trademark Office Re. U.S. Appl. No. 11/798,017.
Official Action Dated Mar. 15, 2004 From the US Patent and Trademark Office Re.: U.S. Appl. No. 09/765,316.
Official Action Dated Dec. 19, 2012 From the US Patent and Trademark Office Re. U.S. Appl. No. 12/448,473.
Official Action Dated Dec. 28, 2012 From the US Patent and Trademark Office Re.: U.S. Appl. No. 10/343,792.
Official Action Dated Nov. 30, 2012 From the US Patent and Trademark Office Re. U.S. Appl. No. 12/514,785.
Response Dated Apr. 7, 2009 to Official Action of Oct. 7, 2008 From the US Patent and Trademark Office Re.: U.S. Appl. No. 10/616,301.
Response Dated Jan. 27, 2011 to Official Action of Nov. 1, 2010 From the US Patent and Trademark Office Re.: U.S. Appl. No. 12/728,383.
Summons to Attend Oral Proceedings Pursuant to Rule 115(1) EPC Dated Nov. 29, 2012 From the European Patent Office Re. Application No. 06756259.5.
Supplementary European Search Report and the European Search Opinion Dated Nov. 13, 2012 From the European Patent Office Re. Application No. 06728347.3.
Berman et al. "Dual-Isotope Myocardial Perfusion SPECT With Rest Thallium-201 and Stress Tc-99m Sestamibi", Nuclear Cardiology, 12(2): 261-270, May 1994.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.

Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.

Charland et al. "The Use of Deconvolution and Total Least Squares in Recovering a Radiation Detector Line Spread Function", Medical Physics, 25(2): 152-160, Feb. 1998. Abstract Only!

Chengazi et al. "Imaging Prostate Cancer With Technetium-99m-7E11-C5.3 (CYT-351)", Journal of Nuclear Medicine, 38: 675-682, 1997.

GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.

Jan et al. "Preliminary Results From the AROPET", IEEE Nuclear Science Symposium Conference Record, Nov. 4-10, 2001, 3: 1607-1610, 2001.

Lange et al. "EM Reconstruction Algorithms for Emission and Transmission Tomography", Journal of Computer Assisted Tomography, 8(2): 306-316, Apr. 1984.

Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.

McJilton et al. "Protein Kinase C? Interacts With Bax and Promotes Survival of Human Prostate Cancer Cells", Oncogene, 22; 7958-7968, 2003.

Ohno et al. "Selection of Optimum Projection Angles in Three Dimensional Myocardial SPECT", IEEE Nuclear Science Symposium Conference Record 2001, 4: 2166-2169, 2001.

Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.

Rockmore et al. "A Maximum Likelihood Approach to Emission Image Reconstruction From Projections", IEEE Transactions on Nuclear Science, 23(4): 1428-1432, Aug. 1976.

Seret et al. "Intrinsic Uniformity Requirements for Pinhole SPECT", Journal of Nuclear Medicine Technology, 34(1): 43-47, Mar. 2006.

Shepp et al. "Maximum Likelihood Reconstruction for Emission Tomography", IEEE Transactions on Medical Imaging, MI-1: 113-122, Oct. 1982.

Sitek et al. "Reconstruction of Dynamic Renal Tomographic Data Acquired by Slow Rotation", The Journal of Nuclear Medicine, 42(11): 1704-1712, Nov. 2001.

Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.

Solanki "The Use of Automation in Radiopharmacy", Hospital Pharmacist, 7(4): 94-98, Apr. 2000.

Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.

Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.

Advisory Action Before the Filing of an Appeal Brief Dated Feb. 26, 2013 From the US Patent and Trademark Office U.S. Appl. No. 11/989,223.

Notice of Allowance Dated Feb. 27, 2013 From the US Patent and Trademark Office U.S. Appl. No. 12/514,785.

Official Action Dated Nov. 30, 2012 From the US Patent and Trademark Office U.S. Appl. No. 11/989,223.

Advisory Action before the Filing of An Appeal Brief Dated May 21, 2013 From the US Patent and Trademark Office U.S. Appl. No. 11/980,653.

Applicant-Initiated Interview Summary Dated May 1, 2013 From the US Patent and Trademark Office U.S. Appl. No. 10/343,792.

Applicant-Initiated Interview Summary Dated May 1, 2013 From the US Patent and Trademark Office U.S. Appl. No. 11/980,653.

Applicant-Initiated Interview Summary Dated May 9, 2013 From the US Patent and Trademark Office U.S. Appl. No. 12/448,473.

Notice of Allowance Dated Jun. 14, 2013 From the US Patent and Trademark Office U.S. Appl. No. 10/616,307.

Official Action Dated Jun. 12, 2013 From the US Patent and Trademark Office U.S. Appl. No. 12/087,150.

Bacharach et al. "Attenuation Correction in Cardiac Positron Emission Tomography and Single-Photon Emission Computed Tomography", Journal of Nucelar Cardiology, 2(3): 246-255, 1995.

Uni Magdeburg "Attenuation Map", University of Magdeburg, Germany, Retrieved From the Internet, Archived on Jul. 31, 2002.

Zaidi et al. "Determination of the Attenuation Map in Emission Tomography", Journal of Nuclear Medicine, 44(2): 291-315, 2003.

* cited by examiner

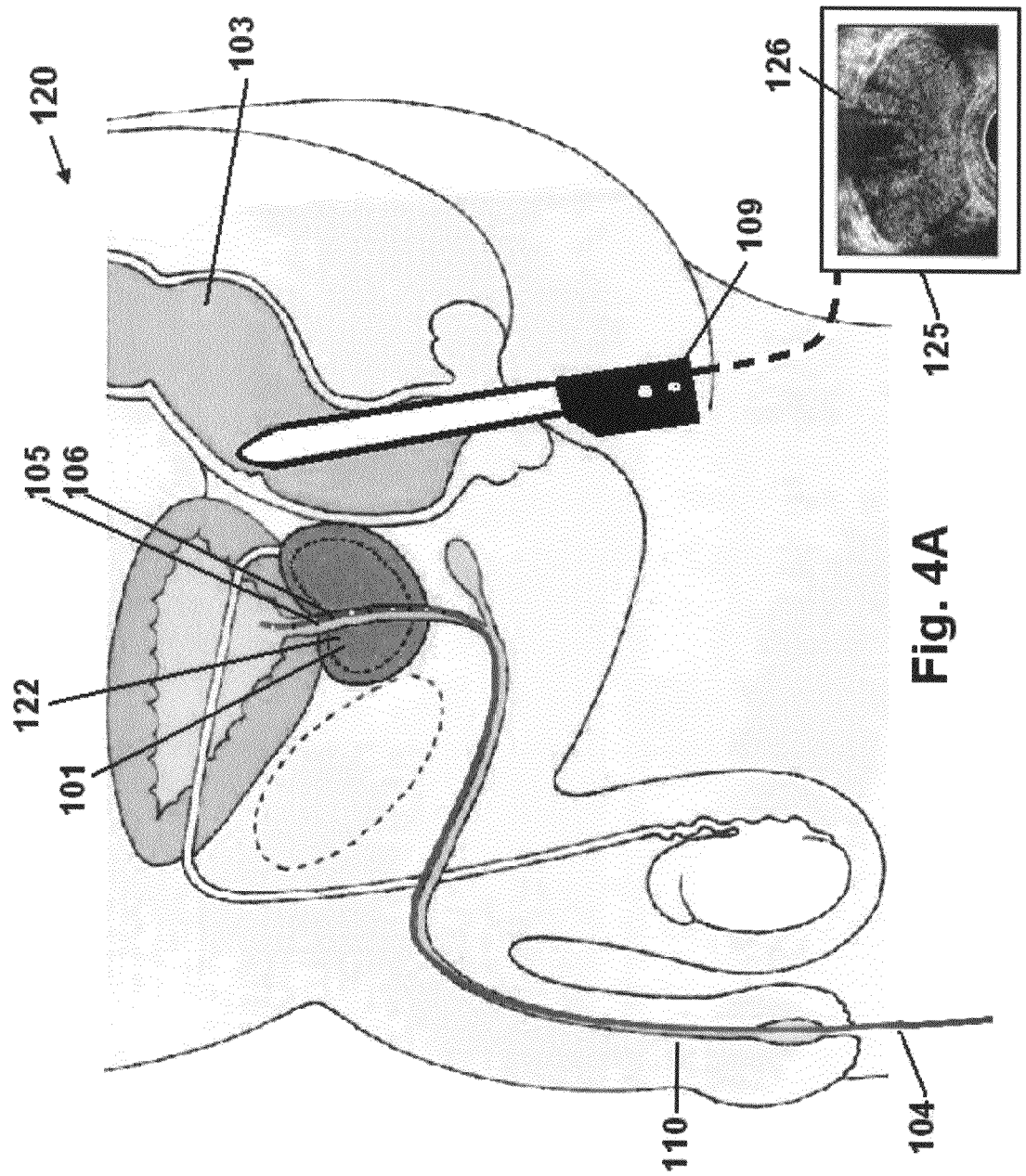

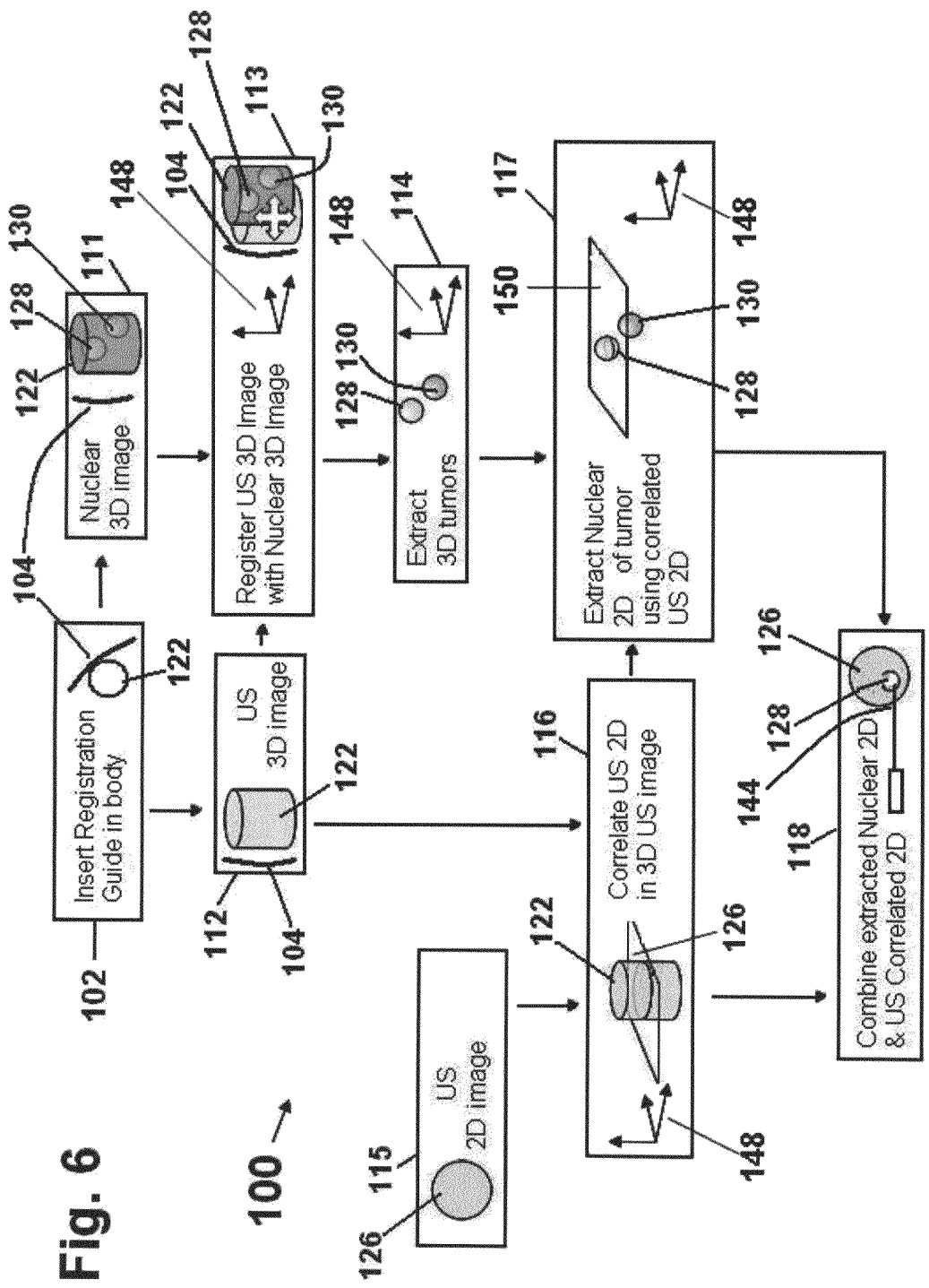

PROSTATE IMAGING

FIELD AND BACKGROUND OF THE INVENTION

The present invention relates to a device and method for registering prostate images, using a registration element suitable for insertion into a body passageway.

The prostate gland may contain multiple tumors that require taking biopsies of multiple tissue samples to determine, for example, the presence of malignant cells.

During prostate biopsy, an ultrasound probe is inserted into the patient rectum to produce ultrasound images of the prostate. A thin biopsy needle is inserted, for example transrectally, and visualized on the ultrasound monitor. The multiple random tissue samples taken with the biopsy needle are sent to a laboratory and analyzed for malignant cells.

To take multiple samples on a non-random basis, nuclear images of the prostate taken from a nuclear imager mounted on a large gantry in close proximity to the surgical field are registered with the ultrasound images.

SUMMARY OF THE INVENTION

According to one aspect of the invention, there is provided a device for registering prostate images, the device comprising: an elongate element suitable for insertion into a body passageway, the elongate element comprising at least one marker readable by an ultrasound probe, and at least one marker readable by a gamma camera.

In embodiments, the elongate element is configured for insertion into a portion of a urethra. In embodiments, the elongate element is flexible.

In embodiments, the at least one marker readable by the ultrasound probe comprises at least one of: air bubbles and solid-state markers.

In embodiments, the at least one marker readable by the ultrasound probe has a different density than the average density of prostate tissue.

In embodiments, the elongate element is provided in a kit containing a tumor imaging fluid and the at least one marker readable by the gamma camera has a photo peak energy that is different from a photo peak energy of the tumor imaging fluid.

In embodiments, the at least one marker readable by an ultrasound probe comprises at least two markers readable by the ultrasound probe and the at least one marker readable by the gamma camera is configured as an interleaf between the at least two of the markers readable by the ultrasound probe.

In embodiments, the device includes at least three interleafs along at least a portion of the elongate element, comprising: at least one first interleaf pattern, at least one second interleaf pattern, and at least one third interleaf pattern.

In embodiments, the at least one first interleaf is spaced a first distance from the at least one second interleaf, and the at least one second interleaf is spaced a second distance from the at least one third interleaf, wherein the first distance is different from the second distance.

In embodiments, the device includes at least two markers readable by the gamma camera, comprising at least one first marker readable by the gamma camera having a different photo peak energy than the at least one second marker readable by the gamma camera.

In embodiments, the device includes at least two markers readable by the ultrasound probe, comprising a first marker having a first density readable by the ultrasound probe and a second marker having a second density readable by the ultrasound probe.

In embodiments, the device includes at least one marker that is readable by the ultrasound probe and the gamma camera.

In embodiments, the device includes at least two markers that are readable by the ultrasound probe and the gamma camera, comprising at least one first marker having a first photo peak energy and at least one second marker having a second photo peak energy.

In embodiments, the device includes at least two markers that are readable by the ultrasound probe and the gamma camera, comprising at least one first marker having a first density readable by the ultrasound probe and at least one second marker having a second density readable by the ultrasound probe.

According to a further aspect of the invention, there is provided a method for registering an ultrasound image with a gamma camera image, the method comprising: imaging a tissue portion and an ultrasound-readable marker using a rectally introduced ultrasound probe, imaging the tissue, and a gamma camera-readable marker using a rectally introduced gamma camera, and registering the image using the ultrasound probe and the image using the gamma camera.

In embodiments, the method includes providing the ultrasound-readable marker and the gamma camera-readable marker on a single elongate element.

In embodiments, the tissue portion comprises a prostate.

In embodiments, the method includes superimposing a 2D slice of the imaging using the gamma camera on a correspondingly registered 2D slice of the imaging using the ultrasound.

In embodiments, the method includes guiding a biopsy needle seen on an ultrasound image with the superimposed 2D slice.

According to another embodiment of the invention, there is provided an image registration device, comprising: a correlating circuit configured to correlate a 2D ultrasound image of a tissue portion to a 3D ultrasound image of the tissue portion and a nuclear extraction circuit configured to extract a 2D nuclear image from a 3D nuclear image of the tissue portion, based on the correlation.

In embodiments, the circuitry is programmed using software. In embodiments, the circuitry is preprogrammed with software.

In embodiments, the circuitry is configured to extract the 2D nuclear image using at least two markers, comprising at least one ultrasound-readable marker, and at least one gamma camera-readable marker.

In embodiments, the circuitry is configured to assemble the 3D ultrasound image from multiple 2D ultrasound images of the tissue portion.

In embodiments, the circuitry includes an image generating software module configured to generate a real time image of the correlated 2D ultrasound image and the 2D extracted nuclear image.

The present invention successfully addresses the shortcomings of the presently known configurations by providing a device and method for registering prostate images using a registration element suitable for insertion into a body passageway.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the imaging arts.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit.

Additionally, software for performing selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data.

Optionally, a network connection is provided as well. A display and/or a user input device such as a keyboard or mouse are optionally provided as well.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention of a device and method for registering prostate images, using a registration element suitable for insertion into a body passageway, is herein described, by way of example only, with reference to the accompanying drawings.

Figure 1:
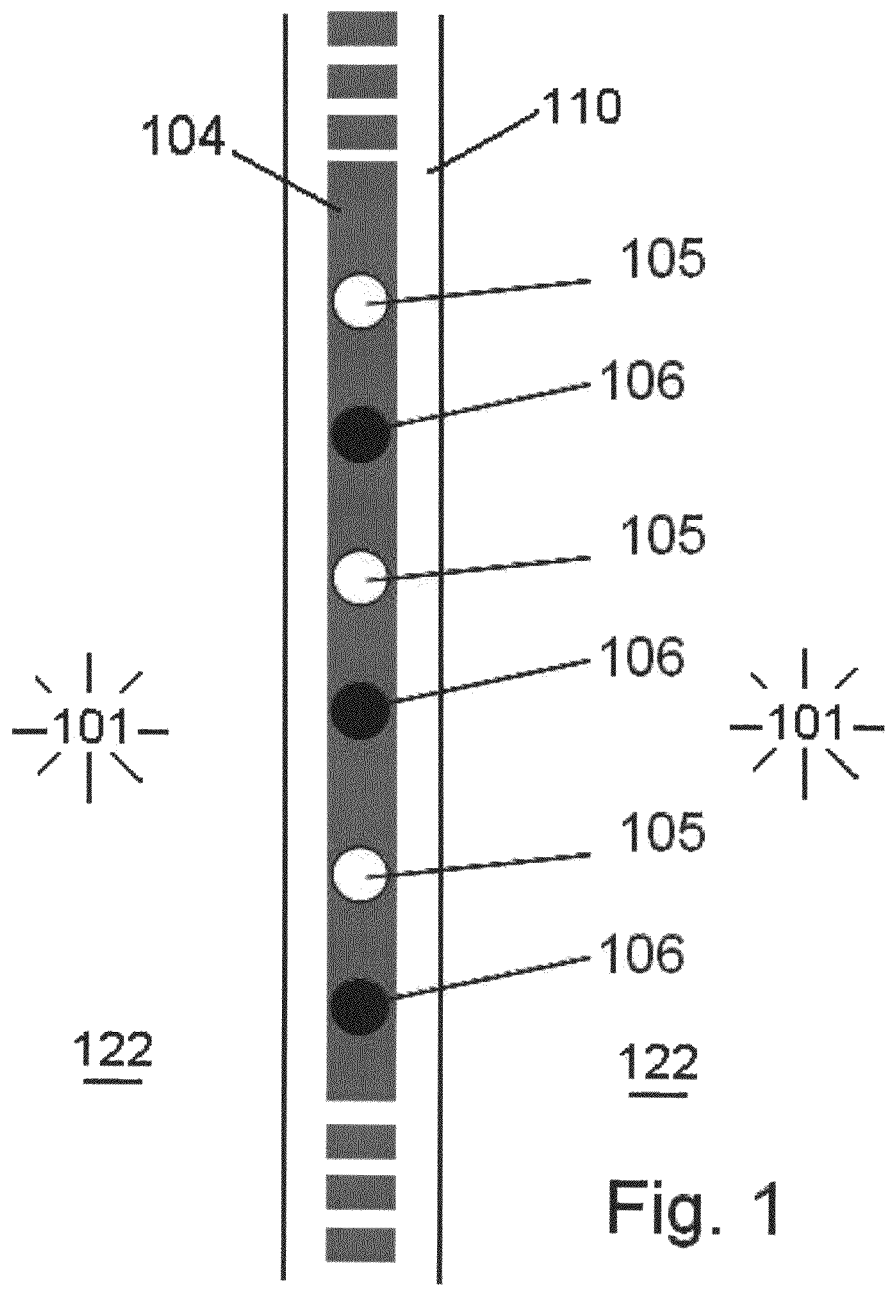

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

In this regard, no attempt is made to show structural details of the invention in more detail than is necessary for a fundamental understanding of the invention; the description taken with the drawings making apparent to those skilled in the art how the several forms of the invention may be embodied in practice.

Figure 2:
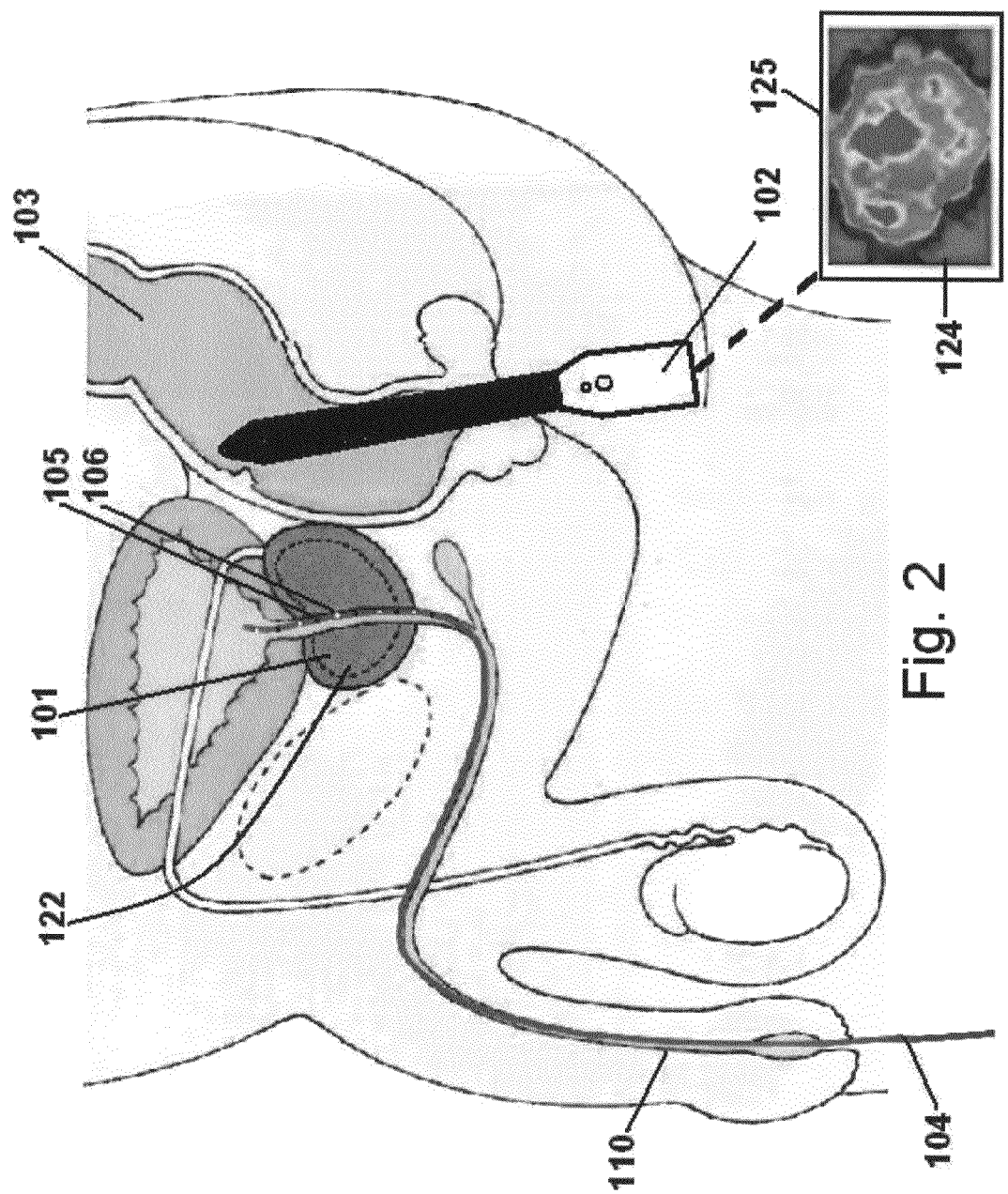
Figure 3:
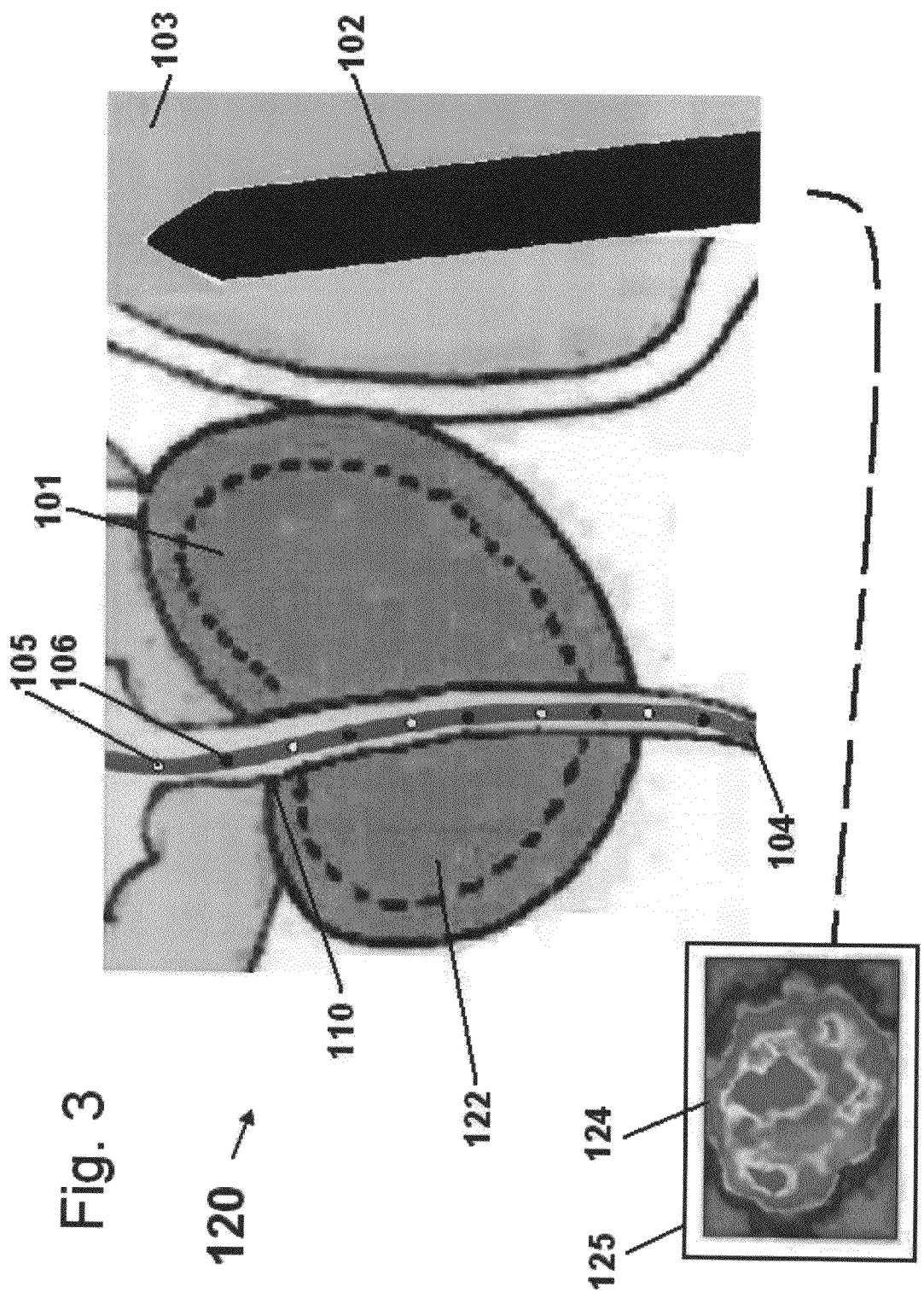
Figure 4B:
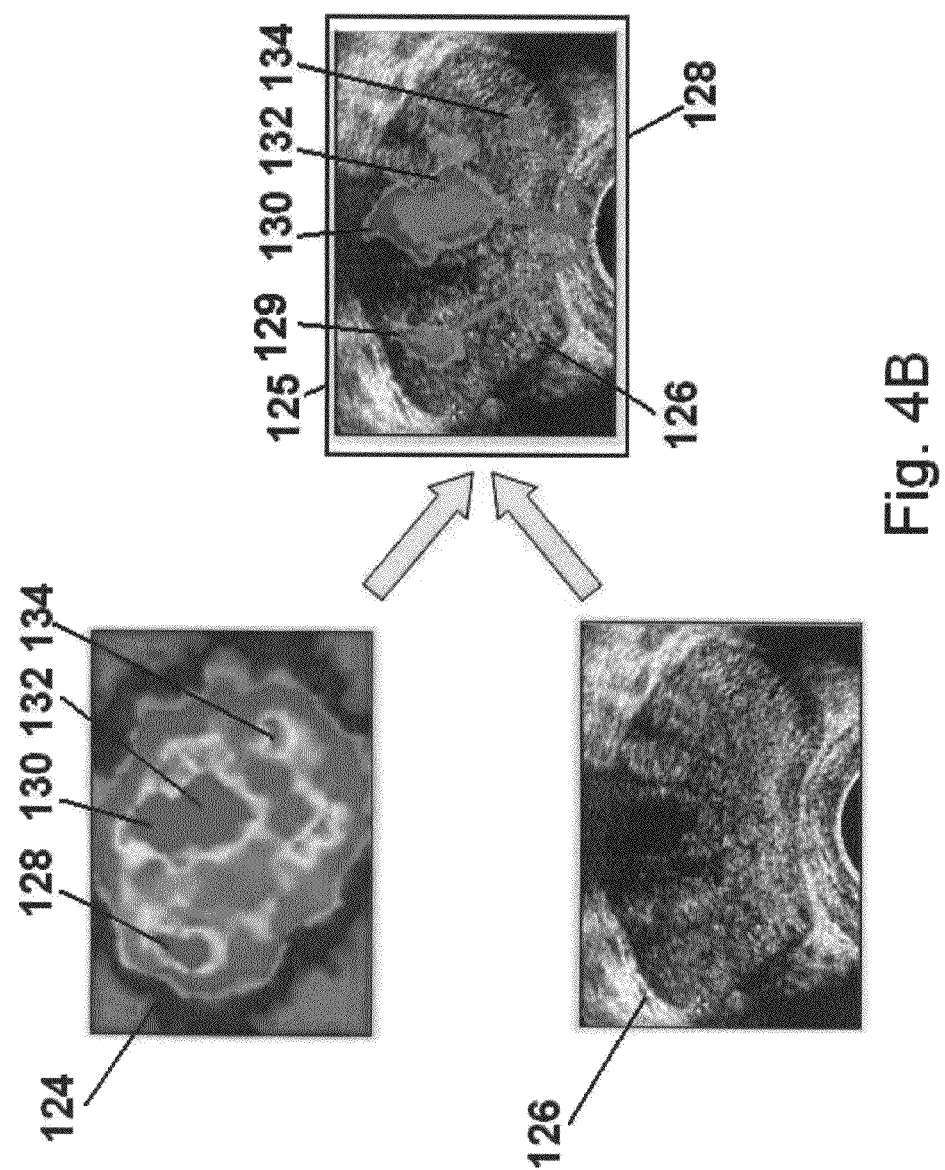
Figure 5:
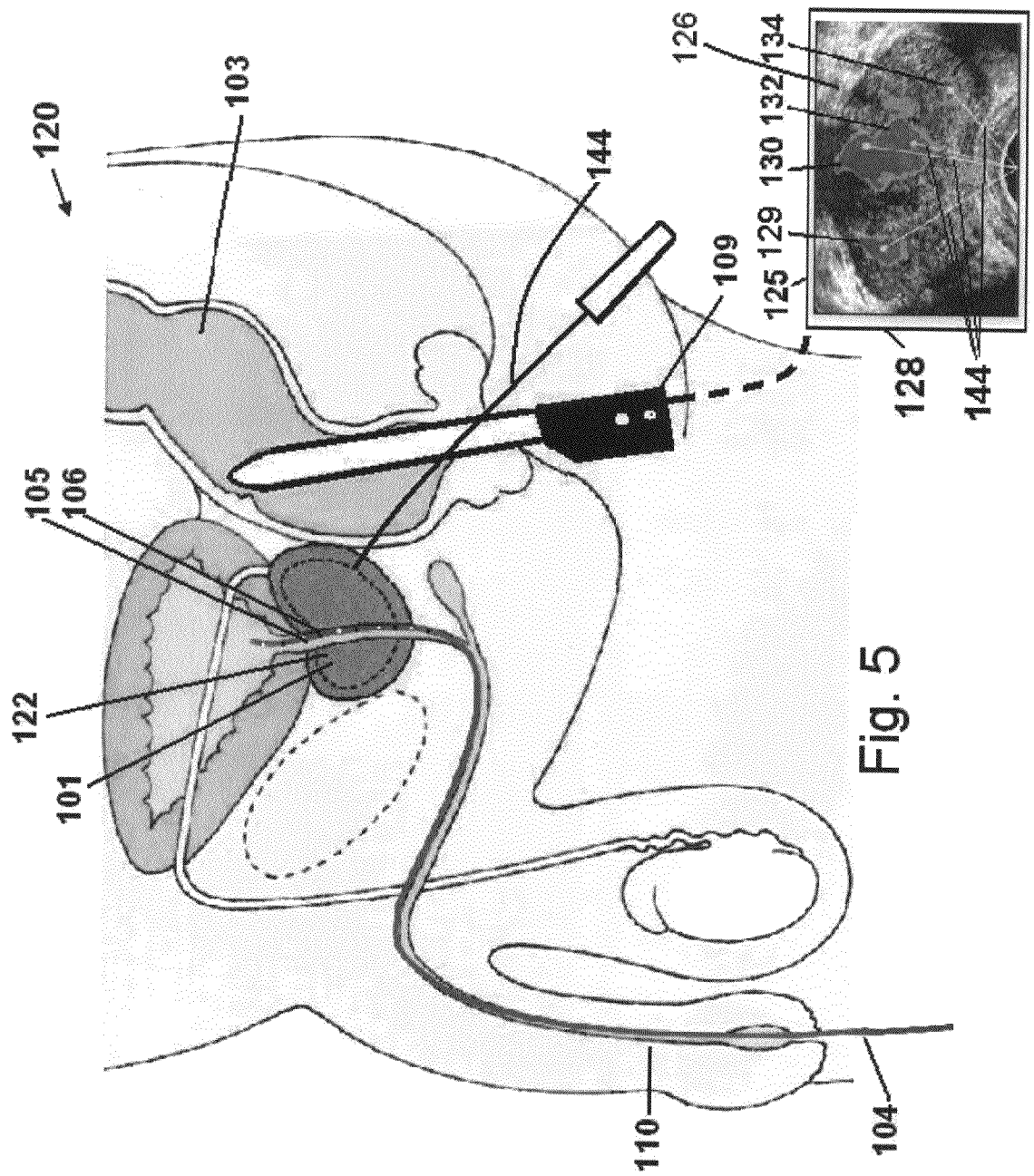

In the drawings:

FIG. 1 shows a registration guide, according to an embodiment of the present invention;

FIGS. 2 and 3 show a gamma camera probe being used to examine a prostate in a cross section of a human body, according to an embodiment of the present invention;

FIG. 4A shows the prostate of FIG. 2 being examined with an ultrasound probe, according to an embodiment of the present invention;

FIG. 4B shows registration of the ultrasound image of FIG. 4A and gamma camera image of FIG. 2, according to an embodiment of the present invention;

FIG. 5 shows biopsies being taken in real time using the registered image of FIG. 4B, according to an embodiment of the present invention; and FIG. 6 shows a Prostate Image Registration Flowchart according to an embodiment of the present invention.

DESCRIPTION OF THE PREFERRED EMBODIMENTS

The present invention is a device and method for providing registration of nuclear and ultrasound images of the prostate in real time.

The principles and operation of the device and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings.

Further, it is to be understood that the invention is not limited in its application to the details set forth in the following description. The invention is capable of other embodiments or of being practiced or carried out in various ways.

In addition, it is to be understood that the phraseology and terminology employed herein is for the purpose of description and should not be regarded as limiting.

Referring now to the drawings:

FIG. 1 shows a registration guide 104 for the registration of ultrasound and nuclear isotope images of prostate tissue 122.

Registration guide 104 comprises a flexible polymer that can easily follow the configuration of a urethra 110 and a diameter that allows easy insertion through urethra 110, for example between about 2.0 and 4.0 millimeters in diameter.

Registration guide 104 includes a nuclear isotope that emits gamma rays that is formed into nuclear imager-readable markers 106. Nuclear imager-readable markers 106 can be formed, for example, by introducing particles of the nuclear isotope into a base comprising a polymer, which is then adhered to registration guide 104.

Nuclear imager-readable markers 106 emit gamma rays having a photo-peak energy that is different from an average photo-peak energy that of an isotope 101 that is introduced by injection. In embodiments, isotope 101 may be introduced as a sub-dermal and/or intra-muscular injection.

In alternative embodiments, isotope 101 may be introduced through vena-puncture. In still other embodiments, isotope 101 may be directly injected into prostate tissue 122 surrounding registration guide 104.

Registration guide 104 additionally includes ultrasound-readable markers 105 comprising air bubbles or solid-state markers that are configured to reflect ultrasound waves.

In embodiments, one or more ultrasound-readable markers have a density that is different from the density of urethra 110 and prostate tissue 122 surrounding registration guide 104. As explained below, there are varieties of arrangements of ultrasound-readable markers 105 and/or nuclear markers 106 on registration guide 104 for the purpose of providing, for example, greater registration precision.

Ultrasound-readable markers 105 and nuclear markers 106 are optionally placed on registration guide 104 to be read by the respective imaging devices from any degree of rotation with respect to registration guide 104.

Referring to FIGS. 2 and 3, prostate isotope 101 has been introduced via the blood stream and absorbed by prostate 122 shown in a cross section of a portion of a human 120.

Registration guide 104, of sufficient length to pass through urethra 110 and prostate 122, is positioned so that ultrasound-readable markers 105 and nuclear imager-readable markers 106 are near prostate 122. A nuclear imager camera probe 102 is placed in a rectum 103 and an image 124 of prostate 122 is acquired and displayed on a monitor 125.

In some cases, it may be advantageous to prevent longitudinal movement of registration guide 104 within urethra 110. In such cases, registration guide 104 optionally includes a balloon at a first end that is inflatable within the bladder and/or a biologically compatible tape that secures a second end of registration guide 104 to the external opening of urethra 110.

Referring to FIG. 4A, nuclear imager camera probe 102 has been replaced by an ultrasound probe 109 in rectum 103.

An ultrasound scan of prostate 122 is made, thereby capturing a long section of registration guide 104, forming an image slice 126 that is displayed on monitor 125. Multiple image slices 126 are formed into a 3D ultrasound image as will be explained below.

In general, the position of nuclear imager camera probe 102 and ultrasound probe 109 are determined by the position of registration guide 104 within the respective images. For example, a portion of registration guide 104 appears in the bottom left corner of an image provided by nuclear imager camera probe 102. The same portion of registration guide 104 appears in the upper right corner of an image provided by ultrasound probe 109. Registration guides in the ultrasound and nuclear images are aligned during processing so that appropriate portions of each image undergo registration.

Optionally, registration guide 104 is a relatively non-stretchable material so that the spacing between ultrasound-readable markers 105 and nuclear imager-readable markers 106 does not significantly change between acquiring images from nuclear imager camera probe 102 and ultrasound probe 109.

Alignment between images from nuclear imager camera probe 102 and ultrasound probe 109 may be optionally enhanced by varying the spacing and/or pattern of ultrasound-readable markers 105 and nuclear imager-readable markers 106.

Registration guide 104 is shown with single ultrasound-readable markers 105 equally spaced between and single nuclear markers 106 that can require capturing a long section of registration guide 104 to provide a basis for image registration.

A greater number of markers 105 and 106 along a given length of registration guide 104 provides for more precise location of images provided by nuclear imager camera probe 102 and/or ultrasound probe 109.

Alternatively, applying groups of markers 105 and 106 and varying parameters of markers 105 and 106 in each group, may allow the operator to more precisely identify the location of each image based upon the positioning of each group of markers.

Variations in parameters may include multiple ultrasound-readable markers 105 that vary in density throughout the length of registration guide 104. Additionally or alternatively, by using different isotopes, multiple nuclear markers 106 may vary in photo-peak throughout registration guide 104, similarly achieving greater imaging precision such that a relatively small field of the imaged portion of prostate 122 can be precisely determined.

Alternatively, to achieve registration precision along a relatively short portion of registration guide 104, ultrasound-readable markers 105 that vary in density and nuclear markers 106 having unvaried photo-peaks may be merged into single markers 105 and 106, thereby providing more precise positioning information.

In still further optional configurations, multiple nuclear markers 106 varying in photo-peak can be merged with ultrasound-readable markers 105.

In still further embodiments, single markers 105 and 106 having variable ultrasound density can be spaced relatively close together.

In still further embodiments to achieve greater positioning precision, ultrasound-readable markers 105 and nuclear markers 106 may be sequenced to form patterns.

For example, an upper portion of registration guide 104 includes two ultrasound-readable markers 105 followed by one nuclear marker 106. Along a mid portion of registration guide 104, two nuclear markers 106 follow one ultrasound-readable marker 105. Along a lower portion of registration guide 104, one nuclear marker 106 is followed by one ultrasound-readable marker 105.

In still further embodiments, variable distances between the markers may be used as a code to support absolute positioning based on relatively short segment of the registration guide.

For example, along an upper portion of registration guide 104, ultrasound-readable markers 105 and nuclear markers 106 are spaced 1 millimeter apart. Along a mid portion of registration guide 104, markers 105 and 106 are spaced 1.5 millimeters apart, while along a lower portion of registration guide 104, markers 105 and 106 are spaced 2.0 millimeters apart.

Referring to FIG. 4B, as seen in image 128, a slice of ultrasound image slice 126 is registered with nuclear image 124, using registration guide 104 to align the images as noted above. Registered image 128 is displayed on monitor 125 in which nuclear markers 106 and acoustical markers 105 have been aligned, merged and then deleted from image 128. Tumors 129, 130, 132 and 134 are shown on ultrasound image 126.

In FIG. 5, registered image 128 is used to visualize the position of biopsy needle 144 in real time and tissue samples are precisely taken from tumors 129, 130, 132 and 134.

FIG. 6 shows a Prostate Image Registration Flowchart 100, which summarizes the steps used in registering the above-noted ultrasound and nuclear images.

Isotope 101 has already been introduced into the patient and has bound to prostate tissue 122 and, with higher density, to prostate tumors 129 and 130.

Beginning at an insert stage 102, registration guide 104 is inserted into the urethra of the patient proximate to prostate 122.

At stage 111, a nuclear camera probe is inserted into rectum 103, and a nuclear image of prostate 122 is acquired. Included in the 3D nuclear image are the images of the above-noted nuclear markers on registration guide 104. The nuclear 3D image is saved for later use and the nuclear camera probe is removed.

At an ultrasound 3D image stage 112, ultrasound probe is inserted into rectum 103 and moved with respect to prostate 122. As the clinician moves the ultrasound probe, position and orientation are recorded with respect to registration guide 104 while a series of 2D ultrasound images are recorded.

These 2D slices, together with the information about their positions and orientations, are formed into an ultrasound 3D image of prostate 122 at ultrasound 3D image stage 112. The captured 3D ultrasound prostate image is saved for later use.

In an image registration stage 113, the 3D nuclear image is registered with the ultrasound 3D image of prostate 122. The registration process registers ultrasound and nuclear images by aligning the appropriate markers on registration guide 104 and a common coordinate system 148 is created for both the ultrasound and nuclear 3D images.

At an optional stage 114, using common image processing methods, the tumors 129 and 130, having higher signal than the background, are distinguished from the background. The background is then deleted from the image. An image of the tumors only, with the registration coordinate system, is saved for a later use.

At an ultrasound 2D stage 115, a real time ultrasound 2D image 126 is taken of the prostate. At a stage 116 the ultrasound 2D image 126 is compared and correlated with the 3D ultrasound image 122 acquired in step 112.

In embodiments, identification of the 2D ultrasound image 126 within the 3D ultrasound image 122 uses a cross correlation method, a feature correlation method, or other methods that may be available in the future.

The location of 2D image 126 is then identified in the common coordinate system 148.

At a stage 117, using the planar information found for 2D image 126 in stage 116 and common coordinate system 148, a correlated 2D slice 150 is extracted from the 3D image saved in stage 114.

In a stage 118, the ultrasound 2D image 126 and the nuclear 2D image 150 are registered using the common coordinate system 148 and displayed on a monitor that includes the real time ultrasound 2D view 126 showing biopsy needle 144 in position with the correlated nuclear 2D view 150 of tumor 129.

Biopsy needle 144, as shown, is entered trans-rectally, however trans-peritoneum or other entry positions are contemplated as well.

It is expected that during the life of this patent, many relevant ultrasound and gamma camera registration systems will be developed and the scope of the term "ultrasound and gamma camera registration systems" is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art.

Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for assisting in registering prostate images, the device comprising:
   an elongate element suitable to follow configuration of a urethra and having a diameter and length allowing insertion into and passing through said urethra to a position near the prostate, said elongate element comprising: i) at least one marker readable by an ultrasound probe, and
   ii) at least one marker readable by a gamma camera;
   wherein said markers and same portions of said elongate element imaged in ultrasound and gamma camera images of the prostate are configured to be aligned in an image registration process.

2. The device according to claim 1, wherein said elongate element is flexible.

3. The device according to claim 1, wherein said at least one marker readable by said ultrasound probe comprises at least one of:
   an air bubble; and
   a solid state marker.

4. The device according to claim 1, wherein said at least one marker readable by said ultrasound probe has a different density than an average density of prostate tissue.

5. The device according to claim 1, wherein said elongate element is provided in a kit containing a tumor imaging fluid and said at least one marker readable by said gamma camera has a photo peak energy that is different from a photo peak energy of said tumor imaging fluid.

6. The device according to claim 1, wherein;
   i) said at least one marker readable by an ultrasound probe comprises at least two markers readable by said ultrasound probe; and
   ii) said at least one marker readable by said gamma camera is configured as an interleaf between said at least two of said markers readable by said ultrasound probe.

7. The device according to claim 6, including at least three interleafs along at least a portion of said elongate element, comprising:
   at least one first interleaf pattern;
   at least one second interleaf pattern; and
   at least one third interleaf pattern.

8. The device according to claim 7, wherein:
   i) said at least one first interleaf is spaced a first distance from said at least one second interleaf; and ii) said at least one second interleaf is spaced a second distance from said at least one third interleaf.

9. The device according to claim 1, including at least two markers readable by said gamma camera, comprising:
   i) at least one first marker having a first photo peak energy; and
   ii) at least one second marker having a second photo peak energy.

10. The device according to claim 1, including at least two markers readable by said ultrasound probe, comprising:
   i) a first marker having a first density readable by said ultrasound probe; and
   ii) a second marker having a second density readable by said ultrasound probe.

11. The device according to claim 1, including at least one marker that is readable by said ultrasound probe and said gamma camera.

12. The device according to claim 1, including at least two markers that are readable by said ultrasound probe and said gamma camera, comprising:
   i) at least one first marker having a first photo peak energy; and
   ii) at least one second marker having a second photo peak energy.

13. The device according to claim 1, including at least two markers that are readable by said ultrasound probe and said gamma camera, comprising:
   i) at least one first marker having a first density readable by said ultrasound probe; and
   ii) at least one second marker having a second density readable by said ultrasound probe.

14. The device of claim 1, wherein said elongate element includes an inflatable balloon at a first end thereof.

15. The device of claim 1, wherein said at least one marker readable by said ultrasound probe and said at least one marker readable by said gamma camera along said elongate element are variably spaced apart or patterned.

16. The device of claim 1,
   wherein along a length of said elongate element at least one said ultrasound probe marker is spaced a distance apart from at least one said gamma camera marker.

17. The device of claim 1, wherein said aligned imaged markers and imaged same portions of said elongate element are used for creating a common coordinate system for said ultrasound and gamma camera images of the prostate.

18. The device of claim 1, wherein the device is used for assisting in acquiring the prostate images.

19. The device of claim 18, wherein a position of said same portions of said elongate element imaged in said ultrasound and gamma camera images of the prostate determines a position of said ultrasound probe and of said gamma camera relative to the prostate.

20. A method for assisting in registering prostate images, the method comprising:
   providing an elongate element suitable to follow configuration of a urethra and having a diameter and length allowing insertion into and passing through said urethra to a position near the prostate, said elongate element comprising: i) at least one marker readable by an ultrasound probe, and ii) at least one marker readable by a gamma camera;
   inserting said elongate element into and through said urethra to a said position near the prostate;
   acquiring ultrasound images and gamma camera images of the prostate and of said markers, by said ultrasound probe and said gamma camera; and
   aligning said markers and same portions of said elongate element imaged in said ultrasound and gamma camera images of the prostate, in an image registration process.

21. The method of claim 20, further comprising using said aligned imaged markers and imaged same portions of said elongate element for creating a common coordinate system for said ultrasound and gamma camera images of the prostate.

22. The method of claim 20, further comprising using a position of said same portions of said elongate element imaged in said ultrasound and gamma camera images of the prostate for determining a position of said ultrasound probe and of said gamma camera relative to the prostate.

* * * * *